(12) United States Patent
Wosmek et al.

(10) Patent No.: US 7,912,551 B2
(45) Date of Patent: Mar. 22, 2011

(54) TELEMETRY NOISE REDUCTION

(75) Inventors: Mark G. Wosmek, Ramsey, MN (US);
James Strom, Arden Hills, MN (US);
John J. Grevious, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 646 days.

(21) Appl. No.: 11/859,041

(22) Filed: Sep. 21, 2007

(65) Prior Publication Data
US 2009/0082833 A1 Mar. 26, 2009

(51) Int. Cl.
*A61N 1/08* (2006.01)
(52) U.S. Cl. .......................................................... 607/60
(58) Field of Classification Search .................... 607/36, 607/60; 128/903, 904
See application file for complete search history.

(56) References Cited

U.S. PATENT DOCUMENTS

| | | | |
|---|---|---|---|
| 1,840,780 A * | 1/1932 | Jones | 343/841 |
| 4,556,063 A | 12/1985 | Thompson et al. | |
| 5,127,404 A | 7/1992 | Wyborny et al. | |
| 5,752,977 A | 5/1998 | Grevious et al. | |
| 6,305,381 B1 * | 10/2001 | Weijand et al. | 128/899 |
| 6,924,773 B1 | 8/2005 | Paratte | |
| 7,035,688 B2 * | 4/2006 | Kast et al. | 607/36 |
| 7,203,549 B2 | 4/2007 | Schommer et al. | |
| 2004/0098068 A1 | 5/2004 | Carbunaru et al. | |
| 2007/0043399 A1 * | 2/2007 | Stevenson et al. | 607/37 |

FOREIGN PATENT DOCUMENTS
EP 1695736 8/2006
* cited by examiner

*Primary Examiner* — Carl H Layno
*Assistant Examiner* — Brian T Gedeon
(74) *Attorney, Agent, or Firm* — John W. Albrecht; Campbell Nelson Whipps LLC

(57) ABSTRACT

A device includes a housing and electronics disposed in the housing. A telemetry antenna is disposed in the housing and is operably coupled to the electronics. A shielding coil is disposed between the housing and the telemetry antenna. The shielding coil has a first end and a second end. The second end is electrically terminated in circuitry of the electronics.

12 Claims, 12 Drawing Sheets

TELEMETRY NOISE REDUCTION

FIELD

This disclosure relates, inter alia, to apparatuses, systems and methods for reducing noise associated with telemetry antennas; particularly for reducing noise associated with telemetry antennas in implantable medical devices.

BACKGROUND

Electromagnetic interference or noise degrades optimum performance of electronic devices. For active implantable medical devices, such as pacemakers, defibrillators, neuromodulators, programmable infusion devices and the like, electromagnetic interference may create potentially dangerous situations. Accordingly, a good deal of care is taken to shield or decouple device electrical components from noise in an effort to maintain a high level of reliable performance.

One source of noise can arise from capacitive coupling between metallic housings of implantable medical devices and inductive coils, such as telemetry antennas, disposed within the housings. Use of the housing as a return electrode for electrical signal generators operating in unipolar mode is one notable source of such noise.

Typically, such sources of noise are minimized by employing conductive spray coating or adhesive conductive shields to surround the inductive telemetry antenna coil in a Faraday cage like manner. However, such materials are often difficult to work with from a manufacturing perspective and may suffer from reliability and variability.

SUMMARY

The present disclosure describes, inter alia, methods, systems and devices that employ a coil shield disposed between a housing and a telemetry antenna. The coil is easier to work with and can produce reproducible results.

In an embodiment, a device is described. The device includes a housing and electronics disposed in the housing. A telemetry antenna is disposed in the housing and is operably coupled to the electronics. A shielding coil is disposed between the housing and the telemetry antenna. The shielding coil has a first end and a second end. The second end is electrically terminated in circuitry of the electronics.

In an embodiment, a method for shielding a telemetry antenna from a housing of an implantable medical device is described. The telemetry antenna is disposed within the housing. The method includes disposing a coil shield between the housing and the antenna and electrically terminating an end of the shielding coil in electronics of the device.

By providing devices, systems and methods that employ a coil as a shield for a telemetry antenna, a simple, reliable and effective mechanism for reducing noise capable of interfering with telemetric performance may be obtained. These and other advantages will be readily understood from the following detailed descriptions when read in conjunction with the accompanying drawings.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used herein, "electrical" interference, interaction, or noise means electrical or magnetic, generally electromagnetic, interference, interaction, or noise.

As used herein "shielding coil" and the like, refer to a wound wire having a plurality of turns and that, in use, acts to shield an electrical component from electrical interference or noise.

The present disclosure describes, inter alia, methods, systems and devices that employ a coil shield disposed between a housing and a telemetry antenna. The coil is easy to work with from a manufacturing perspective and is reliable. Shielding of a telemetry antenna with a coil as described herein has been found to effective in reducing noise.

Figure 1:
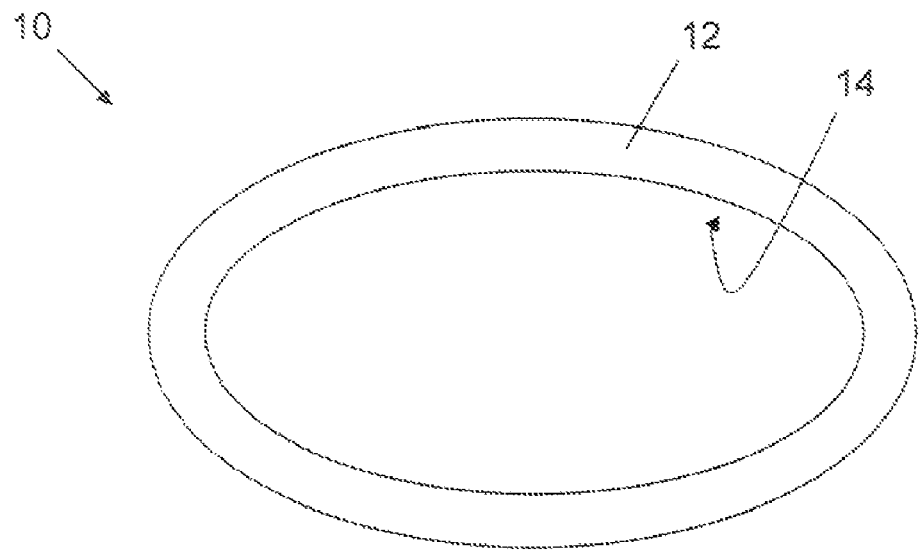
FIG. 1 is a schematic diagram of top view of a representative telemetry antenna coil.
Figure 2:
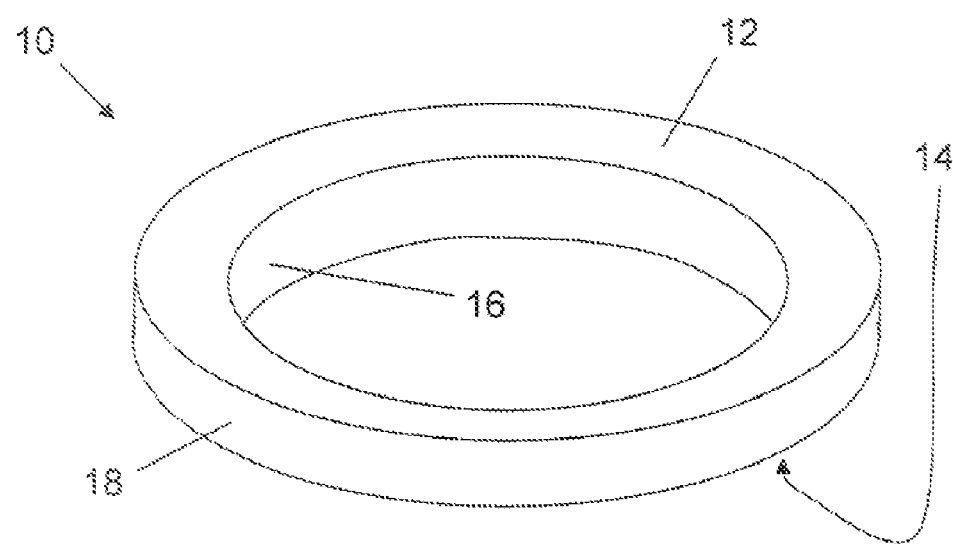
FIG. 2 is a schematic diagram of a perspective view representative telemetry antenna coil.

Referring to FIGS. 1-2, top and perspective views of a telemetry antenna 10 are shown. Telemetry antenna 10 has first 12 and second 14 opposing major surfaces and inner 16 and outer 18 opposing edge surfaces. Telemetry antenna 10 may be any suitable telemetry antenna, such as a wound wire. Telemetry antenna 10 coil wire may be made of copper or other suitable material. In various embodiments, telemetry coil is a low frequency telemetry coil. For example, telemetry coil may operate at a frequency of 200 kHz or less; e.g., at about 175 kHz. Additional information regarding telemetry in general, particularly as it applies to implantable medical devices and systems, can be found in U.S. Pat. No. 4,556,063 to Thompson et al., U.S. Pat. No. 5,752,977 to Grevious et al., and U.S. Pat. No. 5,127,404 to Wyborny et al., which patents are hereby incorporated herein by reference in their respective entireties to the extent that they do not conflict with the disclosure presented herein.

Figure 3:
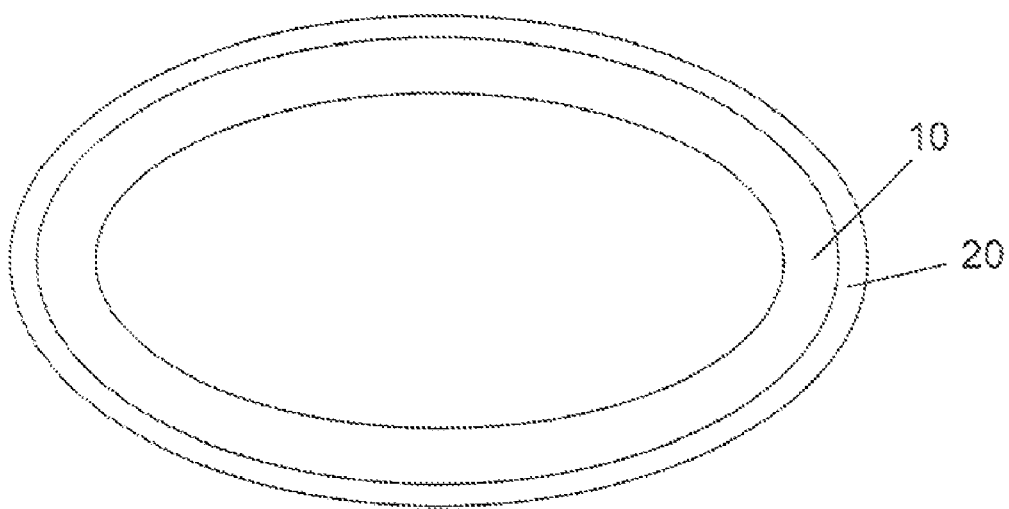
FIG. 3 is a schematic diagram of top view of a representative telemetry antenna coil and shielding coil.
Figure 4:
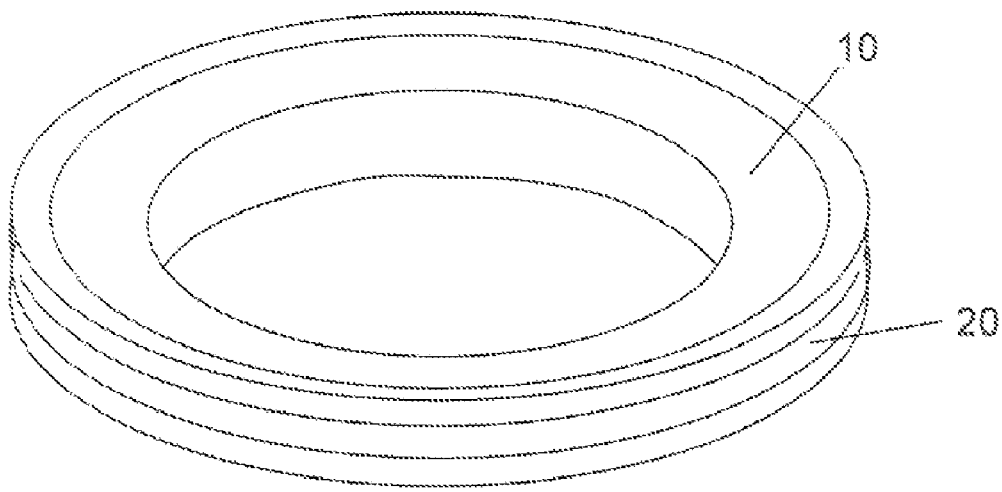
FIG. 4 is a schematic diagram of a perspective view representative telemetry antenna coil and shielding coil.

Referring to FIGS. 3-4, top and perspective views of a shielding coil 10 disposed around a telemetry antenna 10 are shown. Shielding coil 20 comprises a wound wire having a plurality of turns. Shielding coil 20 may be made of any suitable electrically conductive material. For example, shielding coil may be formed from a wire comprising a metallic material. In various embodiments, shielding coil 20 is formed from insulated copper wire. Shielding coil 20 wire may be of any suitable gauge. In various embodiments, shielding coil 20 can be about the same gauge as the telemetry coil 10 gauge to finer gauges that can achieve the desired effect with less cross-sectional area. Shielding coil wire 20 may be insulated via a coating, jacket, sleeve, sheath or the like or any other suitable mechanism.

When wound into a coil, shielding coil 20 wire will preferably have a self resonance frequency that is substantially different from the operating frequency of the telemetry antenna 10 to minimize potential interference. For example, the shielding coil 20 may have a self resonance frequency that is substantially greater than the operating frequency of the telemetry coil 10. For example, shielding coil 20 may have a self resonance frequency that is about three times or more greater than the operating frequency of telemetry antenna 10. In various embodiments, the shielding coil 20 has a self resonance frequency that greater than about 800 kHz. It will be understood that self resonance frequency of the shielding coil 20 will relate to the number of turns in the coil 20, the integral spacing between the wire surfaces and the dielectric constant of the material from which the insulation 20 is made. A greater number of turns, as may be required with finer gauge wire to obtain complete coverage, may tend to result in a self resonance frequency approaching the operating frequency of the telemetry antenna 10 (i.e., more turns may tend to lower the self resonance frequency of coil 20) However, finer gauge wire may be easier to work with from a manufacturing perspective. Thus, ease of manufacturing should be balanced against likelihood of obtaining a shielding coil 20 with a self resonance frequency close to the operating range of the telemetry antenna 10.

Unwanted self-resonance effects of the shielding wire can be minimized by applying reverse winding in a balanced manner to eliminate net coil induction from magnetic field sources; e.g., from external magnetic field sources or from the protected antenna coil when used as a transmit antenna. For example and referring to FIG. 5B, a portion of shielding coil 20 may be wound in one direction and a portion wound in an opposite direction. Preferably, the number of turns in one direction should substantially equal the number of turn in the opposite direction. Ideally, the coil 20 should be interleaved such that each subsequent turn is wound in the opposite direction. However, to balance ease of manufacturing with ideal cancellation effects, it may be desirable to wind the first two or more turns in a first direction, the second two or more turn in a second direction opposite the first direction, the third two or more turns (if applicable) in the first direction, the fourth two or more turns (if applicable) in the second direction, etc.

Figure 5A:
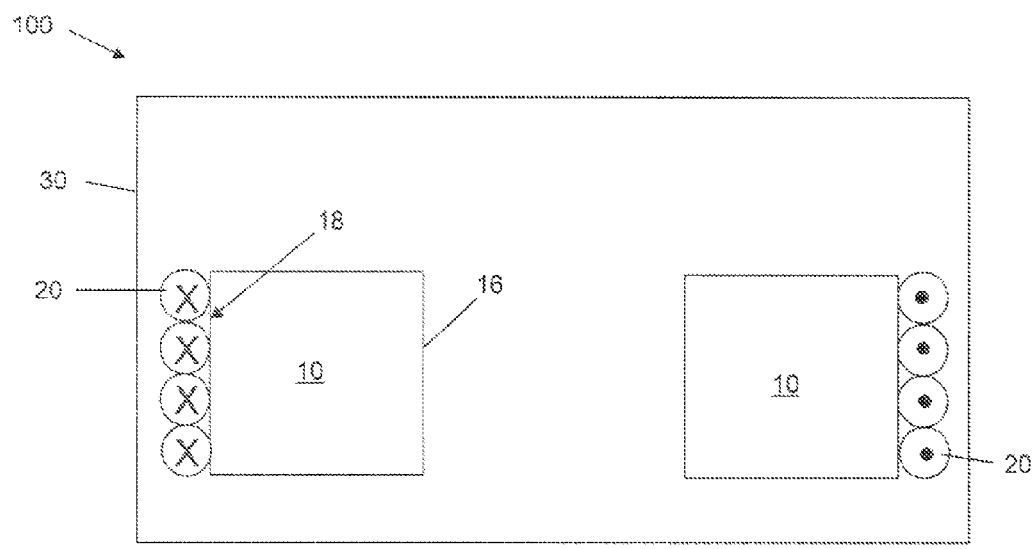
FIG. 5 is a schematic view of a cross-section of a device showing a shielding coil disposed between housing and telemetry antenna.
Figure 5B:
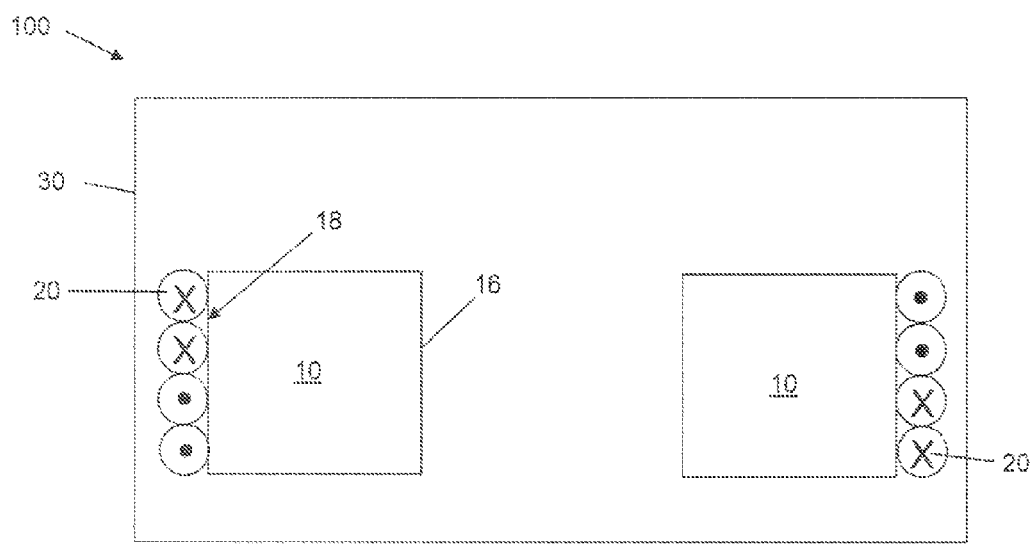
Figure 6:
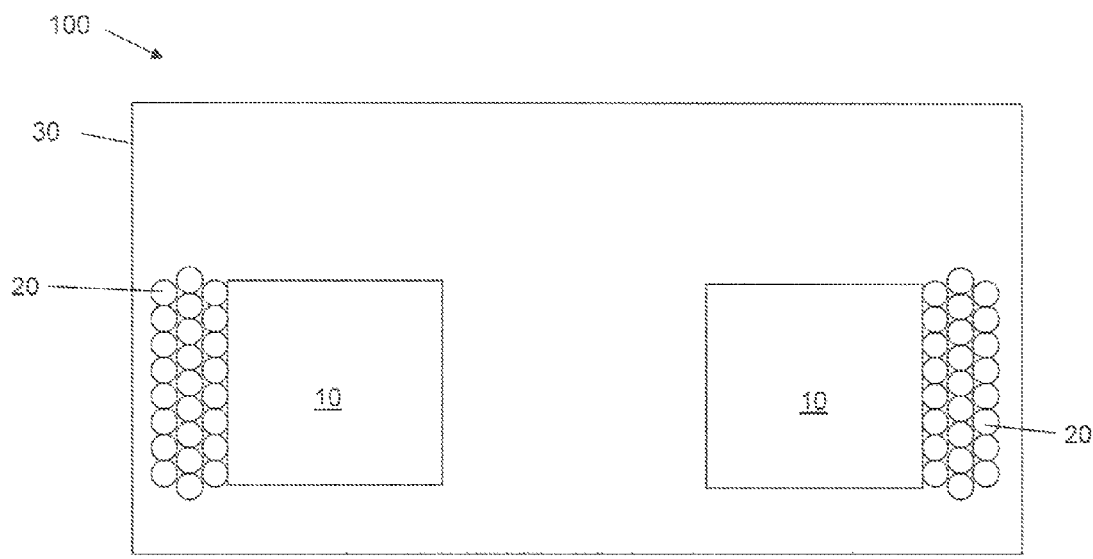
FIG. 6 is a schematic view of a cross-section of a device showing a multiple layer shielding coil disposed between housing and telemetry antenna.

Referring to FIGS. 5-7, schematic diagrams of cross-sections of devices 100 are shown. Practically any device 100 in which electrical interference, e.g. capacitive coupling, may arise due to interaction between housing 30 or other component of device 100 and telemetry antenna 10 may occur will benefit from a shielding coil 20 as described herein. Such devices include key chain remote car locking devices and implantable medical devices operating at low inductive frequencies. Non-limiting examples of implantable medical devices that may be employed in accordance with the teachings provided herein include implantable infusion devices and implantable electrical signal generators, such as cardiac defibrillators, pacemakers, neurostimulators, gastric stimulators, implantable monitoring devices and cochlear implants. As shown in FIGS. 5-7, the device 100 includes a housing 30 in which a telemetry antenna 10 is disposed. The housing 30 contains a material capable of electrically interacting with, e.g. capacitive coupling to, the antenna 10 in the presence of an appropriate electromagnetic field. Typically the housing 10 includes a metallic component. In various embodiments, the housing 30 is formed from titanium.

In the embodiments depicted in FIGS. 5-7, coil shield 20 is disposed between telemetry antenna 20 and housing 30. In the depicted embodiments, coil shield 20 is generally disposed about exterior 18 edge surface of antenna 10. Coil shield 20 may form a single layer coil (see, e.g., FIG. 5) or a multiple layer coil (see, e.g., FIG. 6). Whether the coil shield 20 is a single layer or in multiple layers, the coil 20 is preferably wound to minimize gaps. Multiple layers may provide better assurance to minimize gaps in the coil 20 between housing 30 and antenna 10. It may be desirable for multiple layer coils 20 to be formed from finer gauge wire so that the coil 20 does not take up a large volume of space in the device 100. However, considerations regarding self resonance frequency, as discussed above, should be kept in mind as well.

Figure 7A:
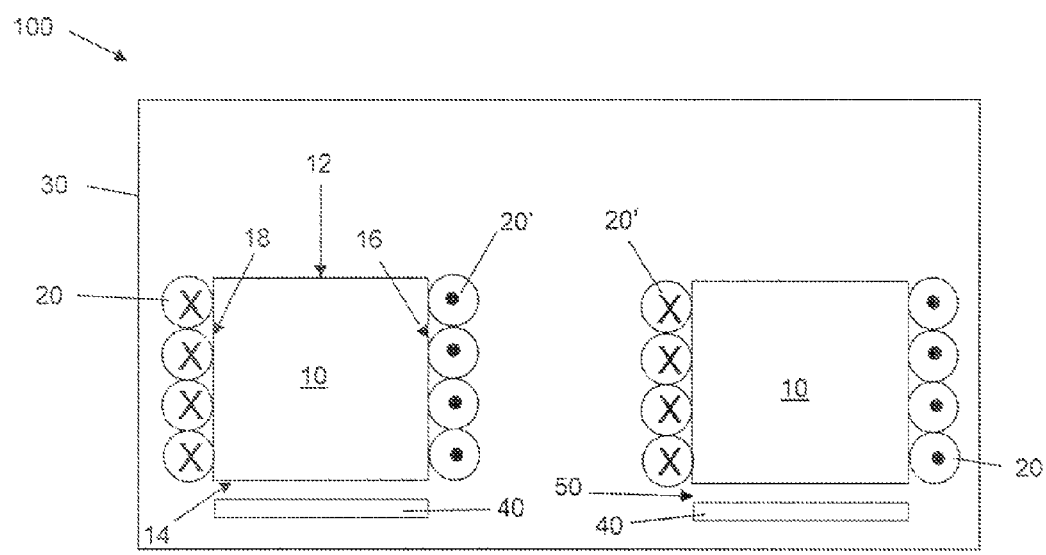
FIG. 7 is a schematic view of a cross-section of a device showing a shielding coil disposed between housing and telemetry antenna, a shielding coil disposed internally to the antenna and a conductive layer disposed under the antenna.
Figure 7B:
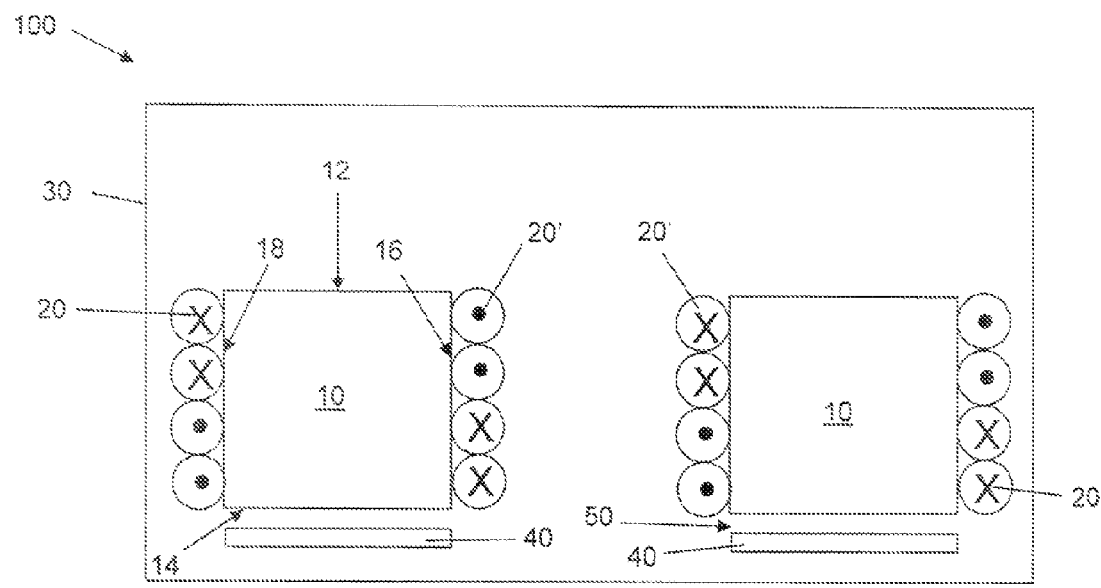

Referring to FIG. 7A, device 100 may include an internal shielding coil 20' to shield antenna 10 from internal components (not shown) of device 100 or other sources of noise. Coil shield 20', in the depicted embodiment, is disposed generally in proximity to inner edge surface 16 of antenna 10. Accordingly, antenna 10 is disposed between internal shielding coil 20' and housing 30. Internal coil 20' may be wound in one direction, while external shielding coil 20 is wound in the opposite direction with equal number of turns in an attempt to achieve a desirable net-zero induced voltage across the shield coil terminals. However, if the area of the internal coil 20' is significantly smaller than the area of the external shielding coil 20, it may be desirable to increase the number of turns (e.g., by using a finer gauge wire) as the voltage induced across an inductive coil is proportional to the number of turns and the areas of the coil. Internal 20' and external 20 coils may be formed from the same wire or may be formed separate wires that are operably coupled. Internal 20' or external 20 coils may be of a single layer or multiple layers. With reference to FIG. 7B, the external coil 20 and the internal shielding coil 20' may each be wound in opposing directions for voltage cancellation effects as discussed above with regard to FIG. 5B.

A conductive layer 40 may be disposed between a major surface 14 of antenna 10 and housing 30. Such a conductive layer 40 may be desirable when a major surface 12, 14 of antenna 10 is disposed in proximity to housing 30. If both opposing major surfaces 12, 14 of antenna 10 are disposed in proximity to housing 30, it may be desirable to dispose a conductive layer 40 between each major surface 12, 14 and housing 30, opposite which may exist electric field noise from, for example, a patient's skin surface. The conductive layer 40 may be any suitable conductive layer such as a coiled wire or conductive material deposited by spray, sputtering, silkscreening or adhesive with a single gap or patterned gaps to prevent induced eddy currents that follow the coil's circular path. Conductive layer 40 may also be disposed relative to antenna 10 such that a gap 50 exists between conductive layer 40 and antenna 10 to further reduce eddy currents by reduced coupling to the shield where mechanical space can be afforded. Gap 50 may be of any size suitable to reduce the eddy currents. For example, gap 50 may be within about 15% of the coil surface width being gapped.

Figure 8:
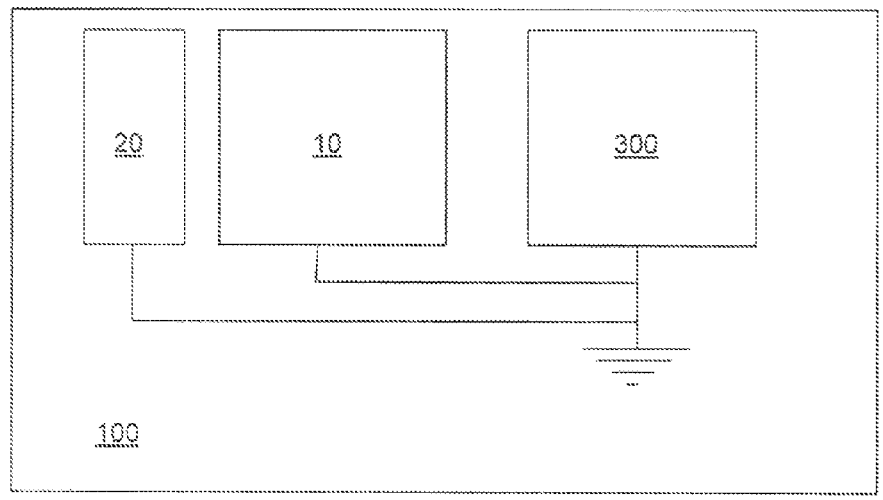
FIG. 8 is a block diagram showing telemetry antenna and shielding coil grounded in electronics of device.
Figure 9A:
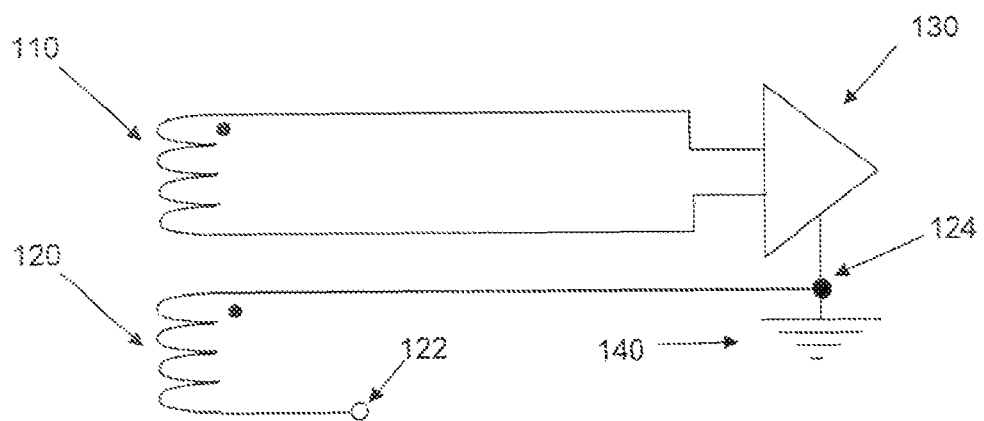
FIGS. 9-14 are schematic diagrams of portions of circuits illustrating representative configurations of shielding coils relative to telemetry antenna coils.
Figure 9B:
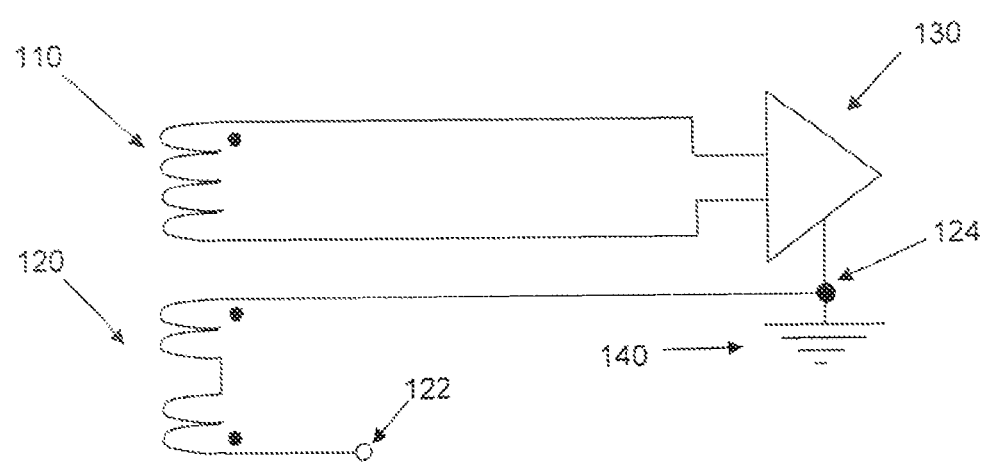

It will be understood that FIGS. 5-7 show only select components of device 100 and that device 100 may include other components necessary or desirable for performing the intended function or other functions of device 100. It will be further understood that coil 20, 20' and conductive layer 40, if any, will be appropriately ground to prevent electrical interaction, e.g. capacitive coupling, between housing 30 and antenna 10. For example, coil 20, 20' and conductive layer 40 may be ground in the electronics 300 of device 100 (see, e.g., FIG. 8).

FIGS. 9-14 are circuit diagrams illustrating representative couplings of telemetry antenna coil 110 and shielding coil 120. While it will be understood that the circuit components shown in FIGS. 9-14 may be disposed within a device in any suitable physical configuration, FIGS. 9-14 will be discussed with reference to components as described regarding FIGS. 5-7. It will be understood that FIGS. 9-14 depict only some components that may be included in a suitable telemetry circuit and that other components such as a capacitor for tuning the frequency of the protected antenna coil 10 may be included but are not shown for sake of convenience and clarity.

Figure 11:
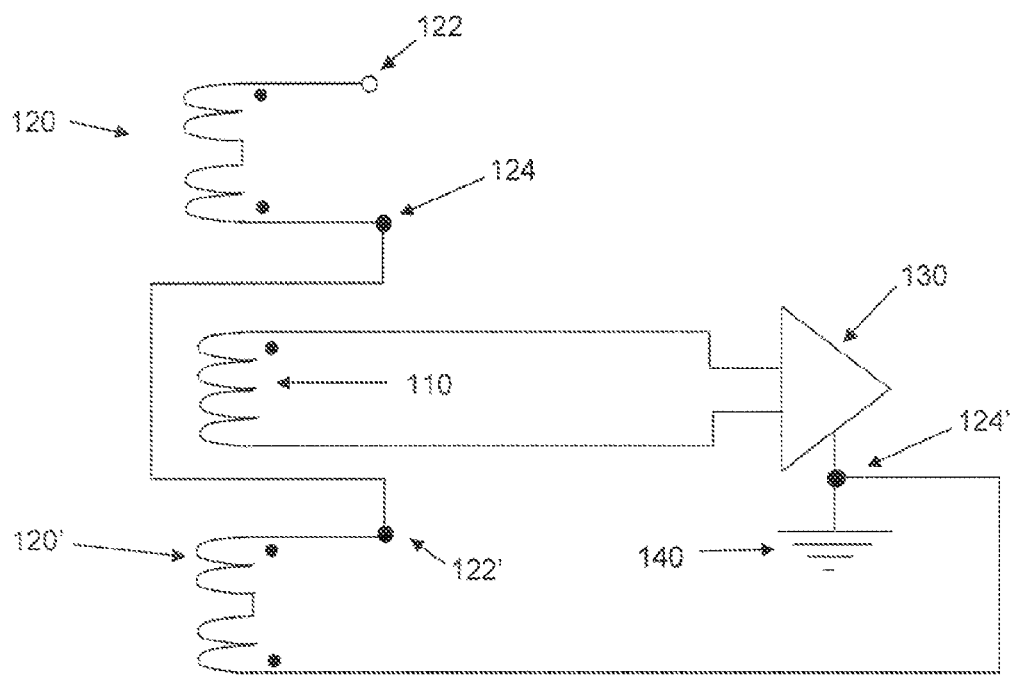
Figure 12:
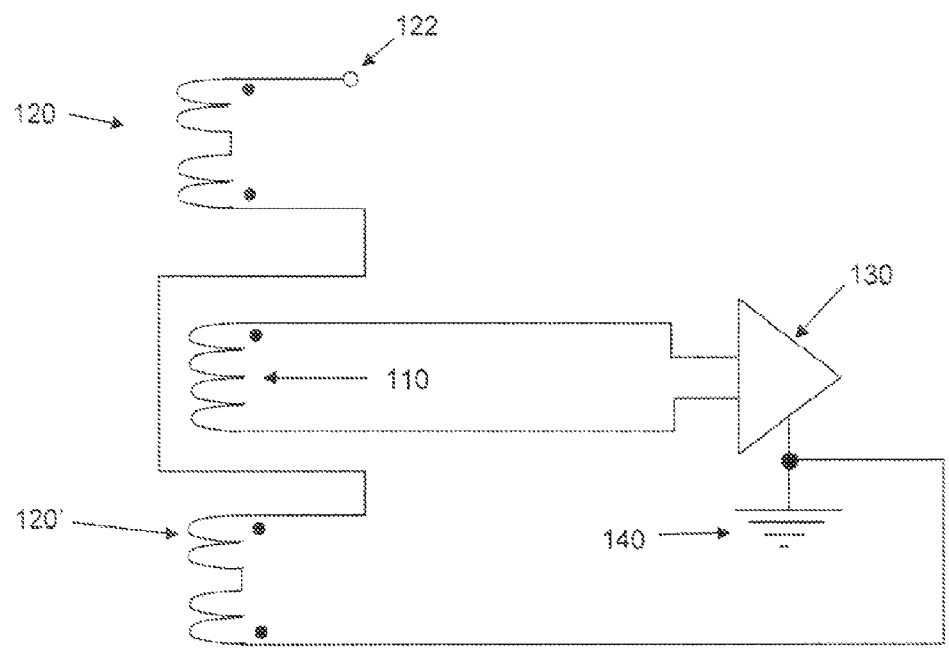
Figure 13:
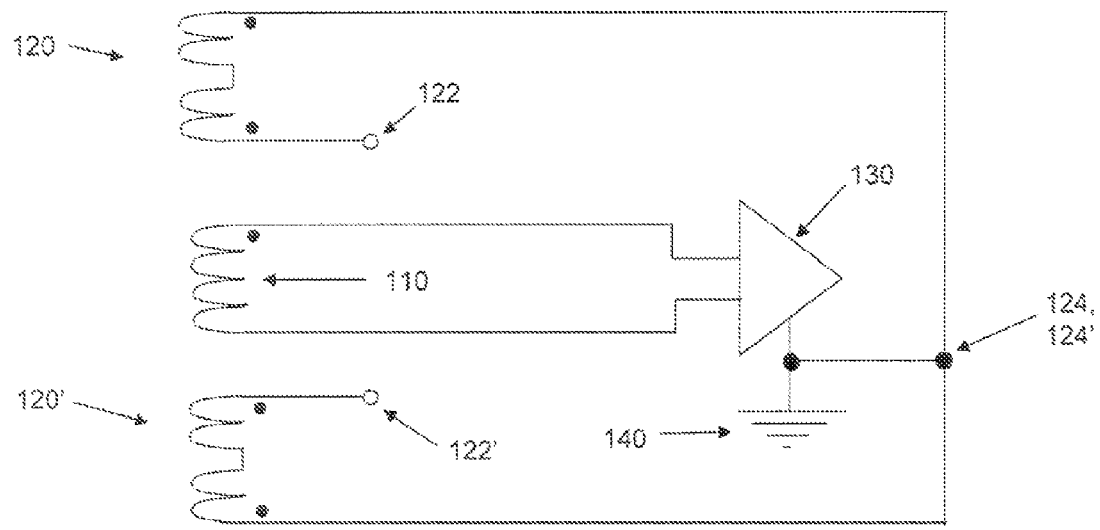
Figure 14:
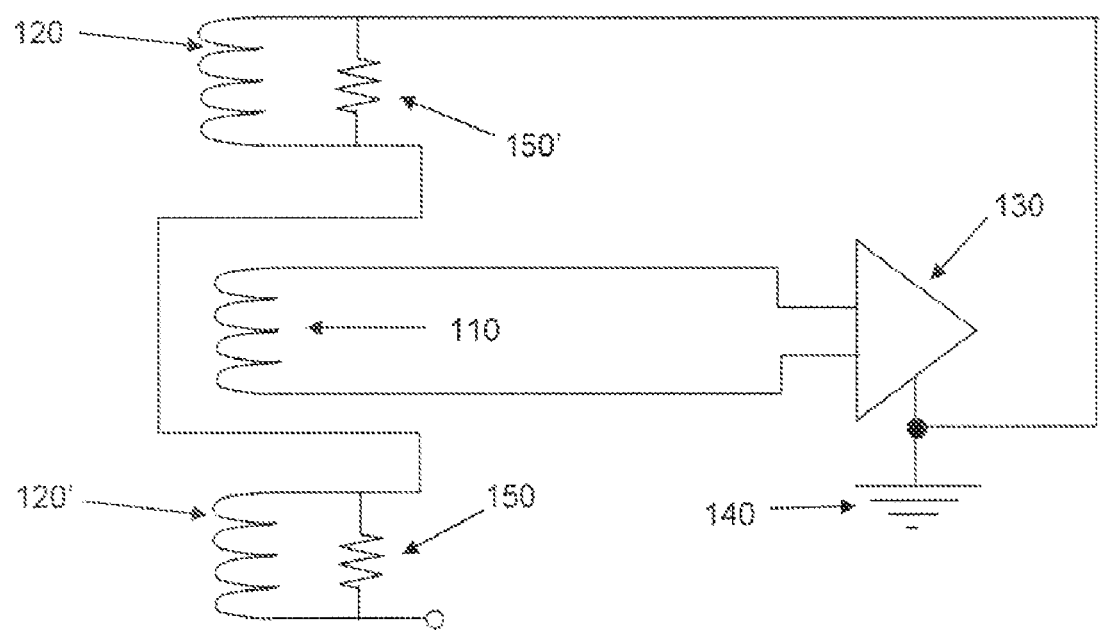

Telemetry antenna 10 forms an inductive coil 110 that is operably coupled to an amplifier 130, such as a differential amplifier, or other suitable circuitry. Amplifier 130, and other associated components (not shown), are terminated in ground 140. Shield coil 20 forms inductive coil 120 and has a first end 122 and a second end 124. The second end 124 of the coil 20 is terminated in ground 140. As shown in FIGS. 11-13, a second shield coil 20' may form a second inductive coil 120'. First 120 and second 120' coils may be formed from a single wire (see, e.g., FIG. 12) or separate wires (see, e.g., FIGS. 11 and 13). If formed from separate wires, the first coil wire 20 has a first end 122 and a second end 124, and the second coil wire 120' has a first end 122' and a second end 124'. The second end 122 of the first shielding coil 120 may be operably coupled to the first end 122' of the second shielding coil 20', and the second end 124' may be terminated in ground 140 (see, e.g., FIG. 11). Alternatively, as depicted in FIG. 13, the second ends 124, 124' of both the first 20 and second 20' may be terminated in ground 140. Of course any other suitable configuration may be employed.

Figure 10:
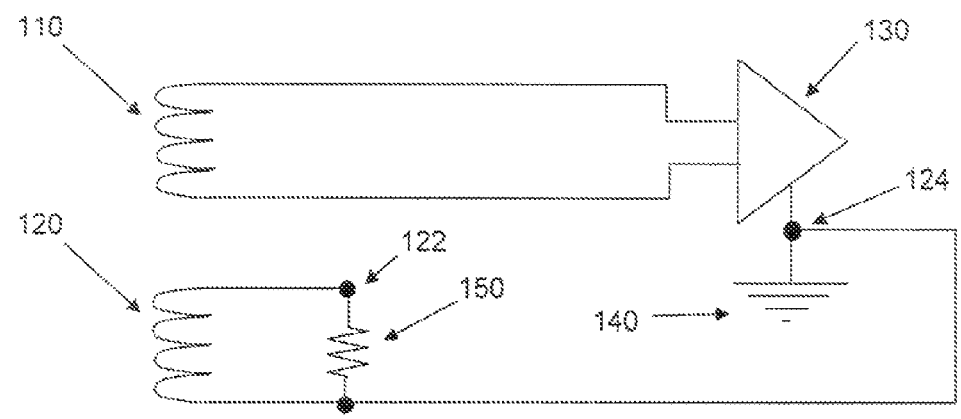

Unwanted shield coil 20, 20' responses can occur due to inductive coupling to the shielded antenna 10 and transient responses to other magnetic fields. One way to address this effect is shown in FIG. 10, where a resistor 150 is be operably coupled to non-cancellation-wound shield coil inductor 120. A suitable resistor may be chosen to provide a desired dampening effect while minimizing undesirable loading of coil 110. By way of example, a resistor having a resistance of about 5 or 10 kohms may be employed. Resistor 150 may be desirably employed when the self resonance frequency of the shield coil forming the inductor 120 approaches the operating frequency of the telemetry antenna. In such circumstances, resistor 150 will lower the self resonant quality Q-factor of the shield coil 20 and thus reduces the degree of unwanted transitent response electrical coupling that may occur between shield inductor 120 and telemetry inductor 110. If more than one inductive shielding coil 120, 120' is employed, additional resistors 150' for the additional coils 120' may be employed, as appropriate (see, e.g., FIG. 14). Alternatively, or in addition, a cancellation-wind maybe employed to minimize unwanted inductive coupling (see, e.g., FIGS. 5B and 9B). The coil 20 is wound in the opposite direction with substantially equal number of turns in an attempt to achieve a desirable net-zero induced voltage across the shield coil 20 terminals. The coil winding sense is indicated by the dot marker in these drawings (see FIGS. 9A-B). This technique is also applied in the embodiments depicted in FIGS. 11, 12 and 13.

Figure 15:
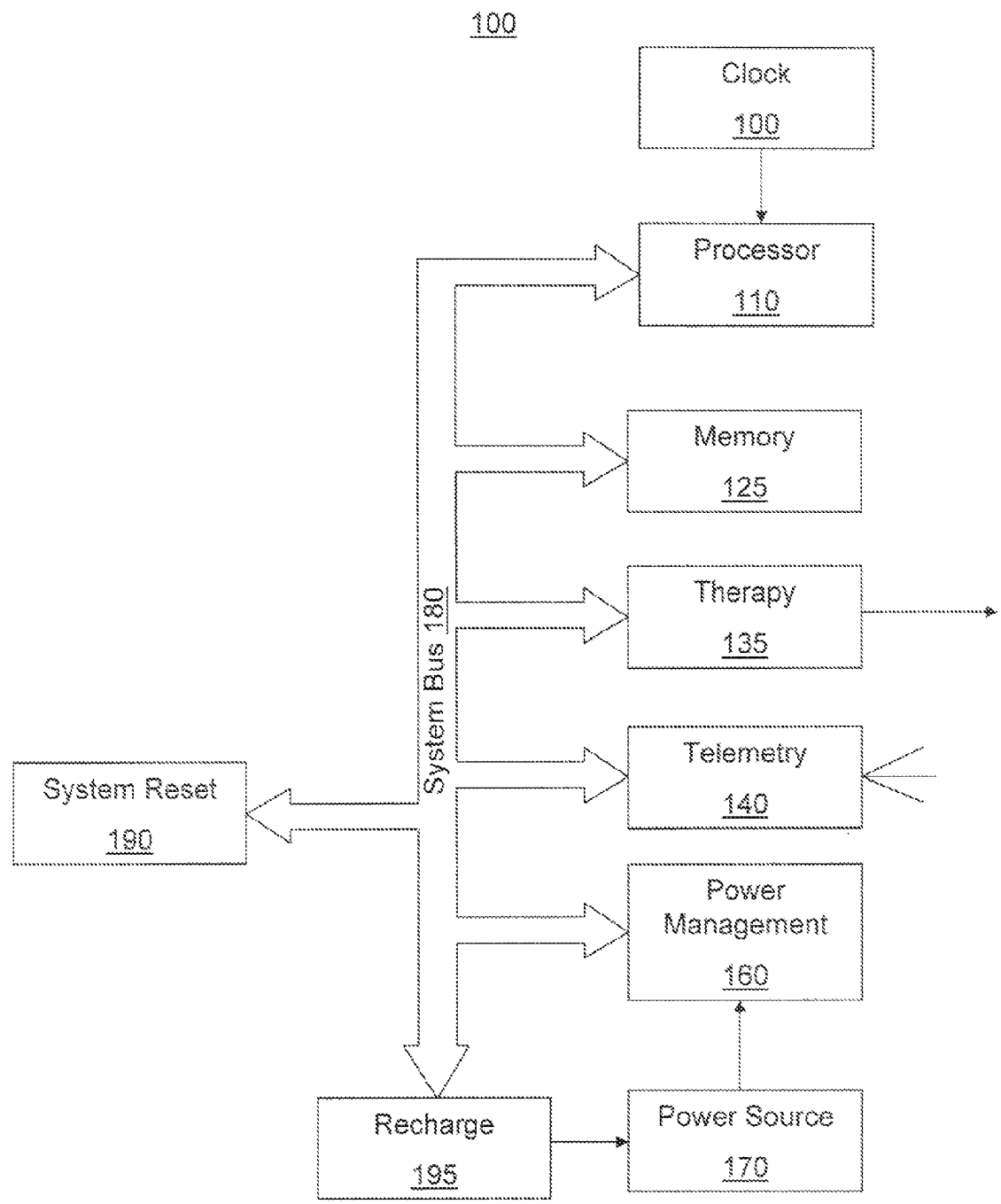
FIG. 15 is a schematic block diagram of components of a representative active implantable medical device.

In various embodiments, device 100 (e.g., as depicted in FIGS. 5-7) is an implantable medical device. Referring to FIG. 15, some representative electronic components of a rechargeable implantable medical device are shown in block form. The various components may be contained in, carried on or connected to housing 30 (see, e.g., FIGS. 5-7). Implantable rechargeable medical device 100 as depicted in the embodiment shown in FIG. 15 includes a clock 100, a processor 110, a memory 125, a therapy output or delivery component 135, a telemetry component 140, a power management module 160, a power source 170, a system reset module 190 and a recharge module 195. Other components of implantable medical device 100 can include, e.g., a diagnostics module, a sensor module, an alert module, or the like (not shown). In the depicted embodiment, all components except the power source 170 can be configured on one or more Application Specific Integrated Circuits (ASICs) or may be one or more discrete components, or a combination of both. Also, all components, except the clock 100 and power source 170 may be connected to bi-directional data bus 180 that is non-multiplexed with separate address and data lines.

Processor 110 may be synchronous and typically operates on low power, such as Motorola 68HC11 synthesized core operating with a compatible instruction set. Clock 100 counts the number of seconds since a fixed date for date/time stamping of events and may be used for therapy control. Memory 125 includes memory sufficient for operation of device 100, such as volatile Random Access Memory (RAM) for example static RAM, nonvolatile Read Only Memory (ROM), Electrically Erasable Programmable Read Only Memory (EEPROM) for example Flash EEPROM, and register arrays configured on ASICs. Direct Memory Access (DMA) is available to selected modules, such as telemetry module 140, so that the selected modules can request control of data bus 180 and write data directly to memory 125 bypassing processor 110. System Reset 190 controls operation of ASICs and modules during power-up of device 100, so ASICs and modules registers can be loaded and brought on-line in a stable condition.

Telemetry 140 module provides for communication between implantable device 20 and external device 40 such as a programmer. Communication may be bi-directional. Telemetry module 140 generally includes a telemetry antenna 10 (see, e.g., FIGS. 1-4), a receiver, a transmitter, and a telemetry processor. Some representative components of telemetry module 140 are depicted in the partial circuit diagrams shown in FIGS. 9-14. Of course other components and circuitry may be employed. Telemetry modules are generally known in the art and are further detailed in U.S. Pat. No. 5,752,977, entitled "Efficient High Data Rate Telemetry Format For Implanted Medical Device" issued to Grevious et al. (May 19, 1998), which is incorporate herein by reference in its entirety to the extent that it does not conflict with the disclosure presented herein.

Therapy module 135 refers to components for carrying out the delivery or generation of therapeutic output to be delivered to a patient from active device 100. One of skill in the art will appreciate that the components may vary on a device-by-device basis and a therapy-by-therapy basis. For example, therapy module 135 may contain an oscillator if device 100 is an electrical signal generator and may contain a pumping mechanism if device 100 is an infusion device.

Figure 16:
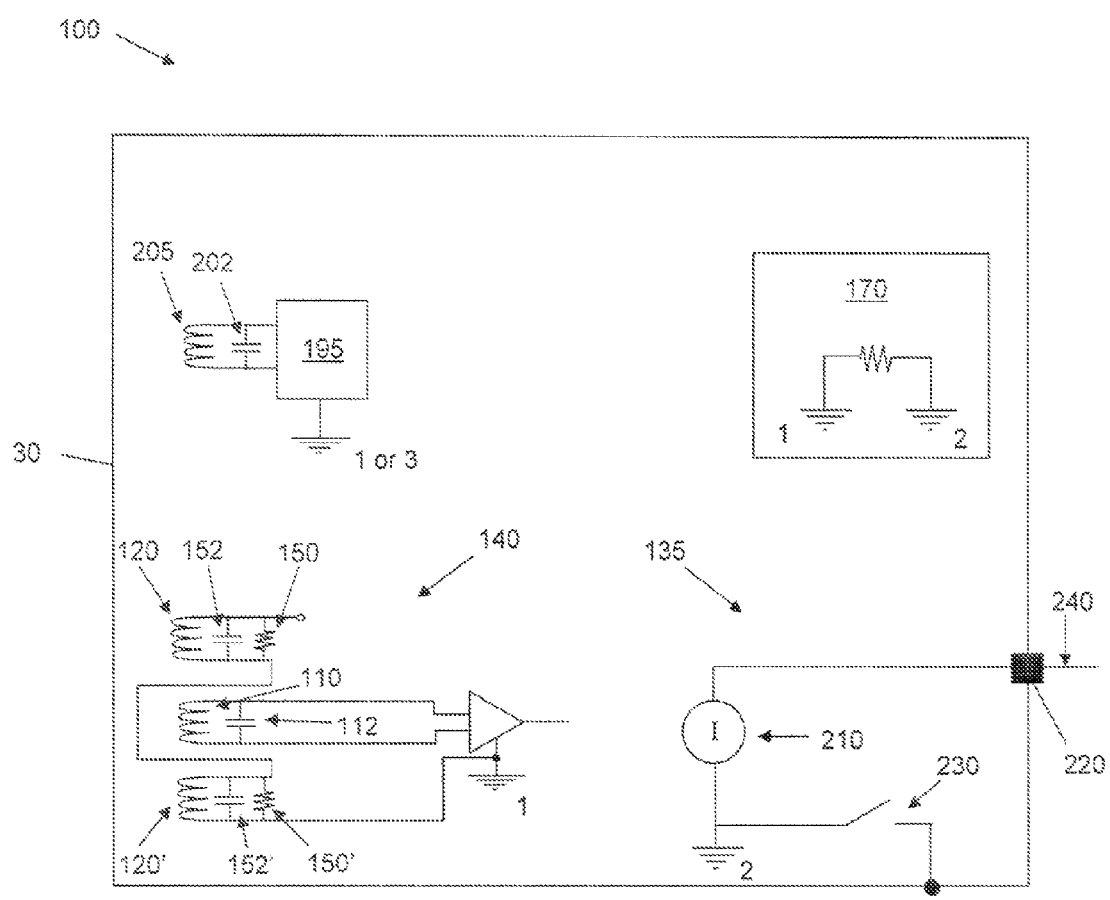
FIG. 16 is a schematic diagram showing representative portions of circuits of an active implantable medical device with a signal generator operating capable of operating in unipolar mode.

Referring to FIG. 16, a schematic diagram showing representative portions of circuits of an active implantable medical device 100 is shown. Device 100 is an implantable signal generator capable of operating in unipolar mode. Device has a hermetically sealed housing 30, and electronics are disposed within the housing 30. The electronics include a power source 170, a recharge module 195, a telemetry module 140, and therapy module 135 capable of generating electrical signals. Of course other electrical components may be present, e.g., as described above. However, for the sake of simplicity and clarity, only selected components are shown. Further only selected portions of the circuits for the selected components are shown for sake of clarity. Other suitable components may readily be included or substituted.

Power source 170 and associated circuitry, in the depicted embodiment, includes two grounds (1, 2) and may include a third or additional grounds. Therapy module 135, in the embodiment depicted in FIG. 16, includes a signal generator 210 and a switch 230 operably coupled to housing 30, which serves as a return electrode for electrical signal delivered to a patient via an electrode of a lead 240. A feedthrough 220 is used to couple lead 240 to signal generator 210 while maintaining the hermetic seal of housing 30. The circuitry of therapy module 135 is terminated in ground 2.

In configurations as depicted, where the housing 30 is used as a return electrode, significant noise can be generated and interfere with operation of telemetry module 140. More particularly, electrical interaction, such as capacitive coupling between the housing 30 and the telemetry antenna, can occur. In such "unipolar" configurations, where the housing 30 is used as return electrode, shielding of the telemetry antenna 10 (see, e.g., FIGS. 1-7) with a shielding coil 20 (see, e.g., FIGS. 3-7) may be particularly desirable.

Telemetry module 140 with associated antenna 10, including inductive coil 110, and shielding coil(s) 20, 20', including inductive coil(s) 120, 120' are terminated in ground 1. Capacitor 112 serves facilitate tuning of telemetry coil inductor 110 to a desired operating frequency.

Recharge module 195 includes recharge antenna forming a coil inductor 205 operably coupled to a capacitor 202 and terminated in ground 1, 3. Recharge circuitry may be terminated in the same ground 1 as the telemetry circuitry or in a different ground 3.

Figure 17:
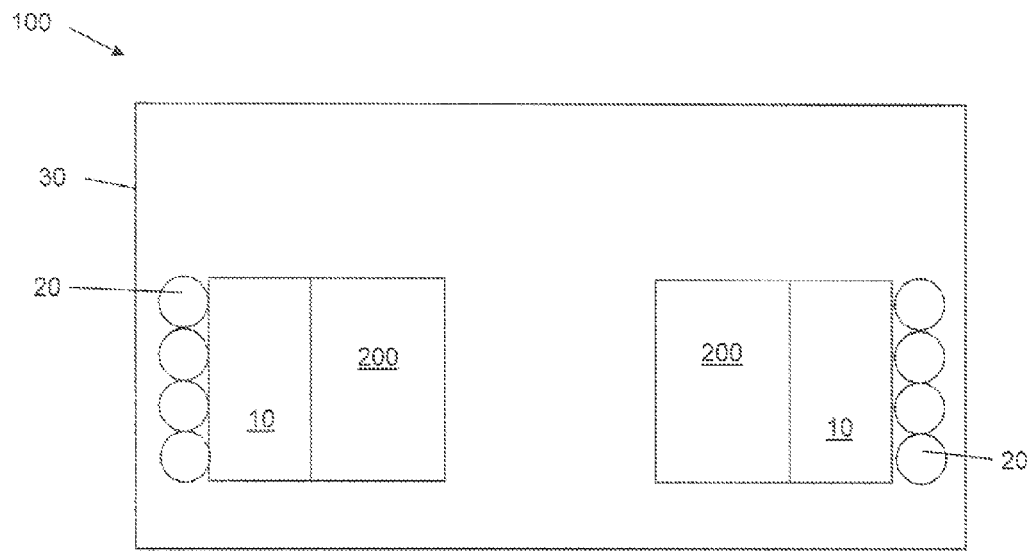
FIGS. 17-18 are schematic diagrams of cross-sections of devices showing housing, recharge coil, telemetry antenna, and shielding coils.
Figure 18:
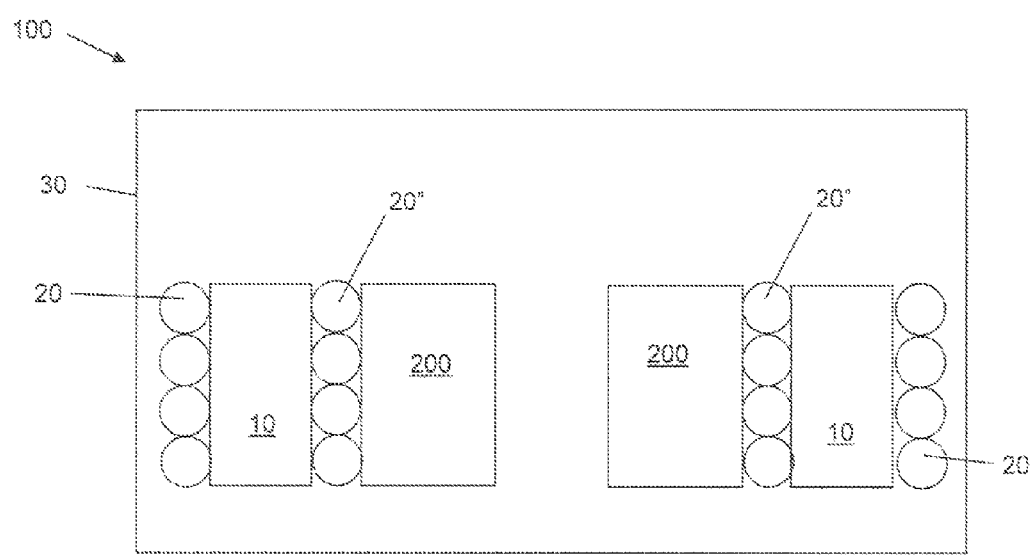

Referring to FIGS. 17 and 18, schematic diagrams of cross-sections of devices 100 illustrating housing 30, recharge coil 200, telemetry antenna 10, and shielding coils 20, 20" are shown. In the depicted embodiments, telemetry antenna 10 is disposed between shielding coil 20 and recharge coil 200, and shielding coil 20 is disposed between housing 30 and telemetry antenna 10. In the embodiment depicted in FIG. 17, the recharge antenna and the telemetry antenna may be operably coupled and thus may share a ground 1 (see, e.g., FIG. 16). Accordingly, shielding coil 20, which may also be terminated in the same ground 1, may serve to shield both telemetry antenna 10 and recharge antenna 200. In the embodiment depicted in FIG. 18, an additional shielding coil 20", which may be formed from the same or different wire that forms the first shielding coil 20, may be disposed between recharge antenna coil 200 and telemetry antenna coil 10. In such configurations, recharge antenna 200 and telemetry antenna 10 may be separately shielded and grounded.

Shielding of a telemetry antenna 10 with a coil shield 20 as described herein has been found to result about a 20 dB reduction in noise. When an internal shielding coil 20' is added along with a conductive layer 40 (see, e.g., FIG. 7), greater than 40 dB noise reduction has been found. The effectiveness of a coil shield, along with its manufacturing ease and reliability, make it a desirable alternative to other conductive shields.

Thus, embodiments of the TELEMETRY NOISE REDUCTION are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device comprising:
a housing;
electronics disposed in the housing;
a telemetry coil antenna disposed in the housing and operably coupled to the electronics; and
a first shielding coil disposed between the housing and the telemetry antenna and having a first end and a second end, the second end being electrically terminated in circuitry of the electronics, wherein the first shielding coil comprises a wound wire having a plurality of turns, wherein the wire is an insulated wire.

2. The device of claim 1, wherein the wire comprises copper.

3. The device of claim 2, wherein the first shielding coil comprises a first turn wound in a first direction and a second turn wound in a direction substantially opposite the first direction.

4. An implantable medical device comprising:
a housing;
electronics disposed in the housing;
a telemetry antenna disposed in the housing and operably coupled to the electronics; and
a first shielding coil disposed between the housing and the telemetry antenna and having a first end and a second end, the second end being electrically terminated in circuitry of the electronics, wherein the first shielding coil comprises a wound wire having a plurality of turns,
wherein the first shielding coil has a self resonance frequency, when wound and disposed in the housing, greater than the telemetry operating frequency.

5. The device of claim 4, wherein the first shielding coil has a self resonance frequency, when wound and disposed in the housing, greater than 175 kHz.

6. An implantable medical device comprising:
a housing;
electronics disposed in the housing;
a telemetry antenna disposed in the housing and operably coupled to the electronics; and
a first shielding coil disposed between the housing and the telemetry antenna and having a first end and a second end, the second end being electrically terminated in circuitry of the electronics, wherein the first shielding coil comprises a wound wire having a plurality of turns,
wherein a resistor is operably coupled to the first shielding coil and is disposed between the first and second ends of the first shielding coil.

7. The device of claim 6, wherein the resistor has a resistance of about 10 kV.

8. An implantable medical device comprising:
a housing;
electronics disposed in the housing;
a telemetry coil antenna disposed in the housing and operably coupled to the electronics;
a first shielding coil disposed between the housing and the telemetry antenna and having a first end and a second end, the second end being electrically terminated in circuitry of the electronics, wherein the first shielding coil comprises a wound wire having a plurality of turns; and
a second shielding coil having a first and second end,
wherein the telemetry antenna is disposed between the second shielding coil and the housing, and
wherein (i) the first end of the second shielding coil is electrically coupled to the second end of the first shielding coil and (ii) the second end of the second shielding coil is electrically terminated in circuitry of the electronics.

9. An implantable medical device comprising:
a housing;
electronics disposed in the housing;
a telemetry antenna disposed in the housing and operably coupled to the electronics; and
a first shielding coil disposed between the housing and the telemetry antenna and having a first end and a second end, the second end being electrically terminated in circuitry of the electronics, wherein the first shielding coil comprises a wound wire having a plurality of turns,
a second shielding coil having a first and second end,
wherein the telemetry antenna is disposed between the second shielding coil and the housing, and
wherein (i) the first end of the second shielding coil is electrically coupled to the second end of the first shielding coil and (ii) the second end of the second shielding coil is electrically terminated in circuitry of the electronics,
wherein the first and second shielding coils are formed of a single wire.

10. An implantable medical device comprising:
a housing;
electronics disposed in the housing;
a telemetry antenna disposed in the housing and operably coupled to the electronics; and
a first shielding coil disposed between the housing and the telemetry antenna and having a first end and a second end, the second end being electrically terminated in circuitry of the electronics, wherein the first shielding coil comprises a wound wire having a plurality of turns,
a second shielding coil having a first and second end,
wherein the telemetry antenna is disposed between the second shielding coil and the housing, and
wherein (i) the first end of the second shielding coil is electrically coupled to the second end of the first shielding coil and (ii) the second end of the second shielding coil is electrically terminated in circuitry of the electronics,
wherein a first resistor is operably coupled to the first shielding coil and is disposed between the first and second ends of the first shielding coil, and wherein a second resistor is operably coupled to the second shielding coil and is disposed between the first and second ends of the second shielding coil.

11. An implantable medical device comprising:
a housing;
electronics disposed in the housing;
a telemetry antenna disposed in the housing and operably coupled to the electronics; and
a first shielding coil disposed between the housing and the telemetry antenna and having a first end and a second end, the second end being electrically terminated in circuitry of the electronics, wherein the first shielding coil comprises a wound wire having a plurality of turns,
a second shielding coil having a first and second end,
wherein the telemetry antenna is disposed between the second shielding coil and the housing, and
wherein (i) the first end of the second shielding coil is electrically coupled to the second end of the first shielding coil and (ii) the second end of the second shielding coil is electrically terminated in circuitry of the electronics,
wherein the telemetry antenna comprises first and second opposing major surfaces and first and second opposing edge surfaces, wherein (i) the first shielding coil is disposed adjacent the first edge surface and (ii) the second shielding coil is disposed adjacent the second edge surface, and wherein a conductive layer is disposed between the first major surface of the antenna and the housing.

12. An implantable medical device comprising:
a housing;
electronics disposed in the housing;
a telemetry antenna disposed in the housing and operably coupled to the electronics, wherein the telemetry antenna is disposed between the recharge coil and the housing;
a first shielding coil disposed between the housing and the telemetry antenna and having a first end and a second end, the second end being electrically terminated in circuitry of the electronics, wherein the first shielding coil comprises a wound wire having a plurality of turns;
a recharge coil operably coupled to the electronics; and
a second shielding coil having a first end and a second end,
wherein the second shielding coil is disposed between the recharge coil and the telemetry antenna, and
wherein (i) the first end of the second shielding coil is electrically coupled to the second end of the first shielding coil and (ii) the second end of the second shielding coil is electrically terminated in circuitry of the electronics.

* * * * *